(12) United States Patent
Wan et al.

(10) Patent No.: US 11,894,108 B2
(45) Date of Patent: Feb. 6, 2024

(54) POTENTIAL ENERGY SURFACE SCANNING METHOD AND SYSTEM FOR MOLECULAR CONFORMATION SPACE ANALYSIS

(71) Applicant: SHENZHEN JINGTAI TECHNOLOGY CO., LTD., Guangdong (CN)

(72) Inventors: Xiao Wan, Guangdong (CN); Mingjun Yang, Guangdong (CN); Li Ouyang, Guangdong (CN); Guangxu Sun, Guangdong (CN); Yang Liu, Guangdong (CN); Jian Ma, Guangdong (CN); Shuhao Wen, Guangdong (CN); Lipeng Lai, Guangdong (CN)

(73) Assignee: SHENZHEN JINGTAI TECHNOLOGY CO., LTD., Guangdong (CN)

( * ) Notice: Subject to any disclaimer, the term of this patent is extended or adjusted under 35 U.S.C. 154(b) by 499 days.

(21) Appl. No.: 17/269,536

(22) PCT Filed: Mar. 6, 2020

(86) PCT No.: PCT/CN2020/078298
§ 371 (c)(1),
(2) Date: Feb. 19, 2021

(87) PCT Pub. No.: WO2021/031550
PCT Pub. Date: Feb. 25, 2021

(65) Prior Publication Data
US 2022/0130492 A1    Apr. 28, 2022

(51) Int. Cl.
*G16C 20/20*    (2019.01)
*G16C 10/00*    (2019.01)

(52) U.S. Cl.
CPC ............. *G16C 20/20* (2019.02); *G16C 10/00* (2019.02)

(58) Field of Classification Search
CPC ................................ G16C 10/00; G16C 20/20
(Continued)

(56) References Cited

U.S. PATENT DOCUMENTS 8,374,828 B1 *   2/2013   Jacobs ................... G16B 15/20
                                                            703/2
11,152,081 B2 *  10/2021  Lario ........................ G16B 5/00
(Continued)

FOREIGN PATENT DOCUMENTS

CN          101131707         2/2008
CN          101647022         2/2010
(Continued)

OTHER PUBLICATIONS

"International Search Report (Form PCT/ISA/210)" of PCT/CN2020/078298, dated Nov. 25, 2020, pp. 1-5.
(Continued)

*Primary Examiner* — Ricky Go
(74) *Attorney, Agent, or Firm* — Muncy, Geissler, Olds & Lowe, P.C.

(57) ABSTRACT

A potential energy surface scanning method and system for the analysis of molecular conformational space includes: judge whether the molecule has adjacent dihedral angles. If there are adjacent dihedral angles, judge whether the adjacent dihedral angles are coupled by QM calculations. If they are judged not to be coupled, then perform one-dimensional potential energy scanning. If judged to be coupled, then perform MM coupling judgment. If the MM calculations determine that the adjacent dihedral angles are not coupled, a one-dimensional potential energy surface scan is performed. If the MM calculation judges that the adjacent dihedral angles are coupled, calculate the coverage of the extreme points on the two-dimensional potential energy surface by the combination of extreme points obtained by
(Continued)

scanning the individual one-dimensional potential energy surfaces of the two dihedral angles according to the MM scanning result. If the coverage is good, then perform one-dimensional potential energy surface scanning.

20 Claims, 3 Drawing Sheets

(58) Field of Classification Search
USPC .......................................................... 702/27
See application file for complete search history.

(56) References Cited

U.S. PATENT DOCUMENTS

| | | | | |
|---|---|---|---|---|
| 2010/0205130 | A1 | 8/2010 | Rohm, III | |
| 2019/0173589 | A1* | 6/2019 | Henningsen | G06F 30/20 |
| 2019/0228842 | A1* | 7/2019 | Jena | G16C 20/80 |
| 2020/0364601 | A1* | 11/2020 | Yamazaki | G06N 10/20 |
| 2021/0098074 | A1* | 4/2021 | Wu | G06N 3/08 |

FOREIGN PATENT DOCUMENTS

| | | |
|---|---|---|
| CN | 102174148 | 9/2011 |
| CN | 104715096 | 6/2015 |
| CN | 110634537 | 12/2019 |

OTHER PUBLICATIONS

"Written Opinion of the International Searching Authority (Form PCT/ISA/237)" of PCT/CN2020/078298, dated Nov. 25, 2020, pp. 1-4.

* cited by examiner

POTENTIAL ENERGY SURFACE SCANNING METHOD AND SYSTEM FOR MOLECULAR CONFORMATION SPACE ANALYSIS

CROSS-REFERENCE TO RELATED APPLICATION

This application is a 371 application of International PCT application serial no. PCT/CN2020/078298, filed on Mar. 6, 2020. The entirety of the above—mentioned patent application is hereby incorporated by reference herein and made a part of this specification.

TECHNICAL FIELD

The invention pertains to the field of conformational analysis, in particular to a potential energy surface scanning method and system for the analysis of molecular conformational space.

BACKGROUND ART

The purpose of conformation analysis is to generate the important conformations of small molecules required for the parameterization of the force field, that is, the low-energy minimum point conformations of the small molecules and the path connecting these conformations (that is, the potential energy surface). For a small molecule containing multiple consecutive dihedral angles, the conformational space increases exponentially with the number of dihedral angles.

Force field development needs to calculate the QM structure and energy of thousands of small molecules, so each small molecule has limited computing resources. 1D scanning is relatively fast and requires less calculation, but for some molecules whose adjacent dihedral angles are not coupled, some important conformations will be missed. 2D scanning is more comprehensive, but the amount of calculation is large, and it is difficult to calculate a large number of molecules. As the number of adjacent dihedral angles of small molecules increases, it becomes impractical to perform two-dimensional or even multi-dimensional scanning. Therefore, the difficulty here is how to use limited computing resources to obtain the most important conformations for a specific small molecule. The potential energy surface of different small molecules is different. Some relatively fast and accurate methods should be used as indicators to judge which potential energy surface scanning can obtain more important conformations for different molecules and better reflect the conformational space of the entire molecule.

DESCRIPTION OF THE INVENTION

Based on the background, it is necessary to provide a potential energy surface scanning method for the analysis of molecular conformational space that can balance efficiency and accuracy.

At the same time, a potential energy surface scanning system for the analysis of molecular conformational space that can balance efficiency and accuracy is provided here.

A potential energy surface scanning method for the analysis of molecular conformational space, including:

Adjacent dihedral angle judgment: judge whether a given molecule has adjacent dihedral angles;

QM coupling judgment: if it is judged that there are adjacent dihedral angles, judge whether the adjacent dihedral angles are coupled through QM calculation, If the QM calculation judges that they are not coupled, perform an one-dimensional potential energy scan: restrain one dihedral angle from $-180°$ to $+180°$ at a set interval, and relax the other dihedral angle, scan to obtain an one-dimensional potential energy surface of the molecule;

If the QM calculation judges that they are coupled, then perform a MM coupling judgment: the MM calculation judges whether the adjacent dihedral angles are coupled;

If MM calculation judges that the adjacent dihedral angles are not coupled, then perform the one-dimensional potential energy surface scan: restrain one dihedral angle to change from $-180°$ to $+180°$ at a set interval and relax the other dihedral angle, scan to obtain the one-dimensional potential energy surface of the molecule;

If the MM calculation judges that the adjacent dihedral angles are coupled, then perform a coverage calculation: calculate a coverage of extreme points on a two-dimensional potential energy surface by a combination of the extreme points obtained by scanning individual one-dimensional potential energy surface of the two dihedral angles according to the MM scanning result; divide coverage levels according to different coverage or coverage ratios as: good, medium and poor;

If the calculated combinations of the extreme points on the two one-dimensional potential energy surfaces have a good coverage for the extreme points on the two-dimensional potential energy surface, then perform the one-dimensional potential energy surface scan: restrain one dihedral angle to change from $-180°$ to $+180°$ at a set interval and relax the other dihedral angle, scan to obtain the one-dimensional potential energy surface of the molecule.

If the combinations of the extreme points on the one-dimensional potential energy surfaces have a poor coverage of the extreme points on the two-dimensional potential energy surface in the coverage calculation, then perform a full two-dimensional potential energy surface scan: restrain the two adjacent dihedral angles simultaneously, and obtain all the combinations of the two from $-180°$ to $+180°$.

If the combinations of the extreme points on the one-dimensional potential energy surfaces have a medium coverage of the extreme points on the two-dimensional potential energy surface in the coverage calculation, then scan a pseudo-two-dimensional potential energy surface: for two adjacent dihedral angles, restrain only one angle is restrained to change from $-180°$ to $+180°$, and, at the same time, the other dihedral angle takes two different starting angle values as starting structure to scan along the potential energy surface of the same dihedral angle.

In a preferred embodiment, the method used in the QM coupling judgment is: for the given molecule with adjacent dihedral angles by a spacing such as $x°$, then the QM energies are calculated by 4 conformers, $(\varphi1, \varphi2)$, $(\varphi1+x, \varphi2)$, $(\varphi1, \varphi2+x)$, $(\varphi1+x, \varphi2+x)$, if ideally coupled, $E(\varphi1+x, \varphi2+x)=E(\varphi1, \varphi2+x)+E(\varphi1+x, \varphi2)-E(\varphi1, \varphi2)$; take a difference between an ideal value and an actual calculated value of $E(\varphi1+x, \varphi2+x)$ as a standard, set a cutoff value, and judge whether the adjacent dihedral angles are coupled.

In a preferred embodiment, the method used in the MM coupling judgment is: carry out MM calculation of the one-dimensional potential energy surface scanning for dihedral angles $\varphi1$ and $\varphi2$ respectively, with one dihedral angle being restrained, set a cutoff value by using the fluctuation range of other dihedral angles to determine whether the adjacent dihedral angles are coupled.

In a preferred embodiment, a cutoff value set in the QM coupling judgment or an absolute deviation of the cutoff value set in the MM coupling judgment is controlled at 2 kcal/mol or a relative deviation is controlled within 5%, and the interval change is 20-40 degrees, if the coverage reaches 80% or above, it is judged as good, and the coverage between 60%-80% is judged as medium, and a coverage below 60% is judged as poor.

A potential energy surface scanning system for the analysis of molecular conformational space, wherein comprising:

Adjacent dihedral angle judgment module: judge whether a given molecule has adjacent dihedral angles;

QM coupling judgment module: if it is judged that there are adjacent dihedral angles, judge whether the adjacent dihedral angles are coupled through QM calculation;

If the QM calculation judges that they are not coupled, perform an one-dimensional potential energy scan: restrain one dihedral angle from $-180°$ to $+180°$ at a set interval, and relax other dihedral angle, scan to obtain the one-dimensional potential energy surface of the molecule;

If the QM calculation judges that they are coupled, then perform a MM coupling judgment: the MM calculation judges whether the adjacent dihedral angles are coupled;

If MM calculation judges that the adjacent dihedral angles are not coupled, then perform the one-dimensional potential energy surface scan: restrain one dihedral angle to change from $-180°$ to $+180°$ at a set interval and relax the other dihedral angle, scan to obtain the one-dimensional potential energy surface of the molecule;

If the MM calculation judges that the adjacent dihedral angles are coupled, then perform a coverage calculation: calculate a coverage of extreme points on a two-dimensional potential energy surface by a combination of the extreme points obtained by scanning individual one-dimensional potential energy surface of the two dihedral angles according to the MM scanning result; divide coverage levels according to different coverage or coverage ratios as: good, medium and poor;

If the calculated combinations of the extreme points on the one-dimensional potential energy surfaces have a good coverage for the two-dimensional potential energy surface, then perform the one-dimensional potential energy surface scan: restrain one dihedral angle to change from $-180°$ to $+180°$ at a set interval and relax the other dihedral angle, scan to obtain the one-dimensional potential energy surface of the molecule.

In a preferred embodiment, if the combinations of the extreme points on the one-dimensional potential energy surface have a poor coverage of the extreme points on the two-dimensional potential energy surface in the coverage calculation calculated in the coverage calculation module, then perform a full two-dimensional potential energy surface scan: restrain two adjacent dihedral angles simultaneously, and obtain all combinations of the two from $-180°$ to $+180°$.

In a preferred embodiment, if the combinations of the extreme points on the one-dimensional potential energy surfaces have a medium coverage of the extreme points on the two dimensional potential energy surface have a medium coverage of the extreme points on the two-dimensional potential energy surface in the coverage calculation calculated in the coverage calculation module, then proceed a pseudo-two-dimensional potential energy surface scanning module: for two adjacent dihedral angles, restrain only one angle to change from $-180°$ to $+180°$, and at the same time, the other dihedral angle takes two different starting angle values as starting structures to scan along the potential energy surface of the same dihedral angle.

In a preferred embodiment, the method used in the QM coupling judgment is: for a molecule with adjacent dihedral angles by a spacing such as $x°$, then the QM energies are calculated by 4 conformers, $(\varphi1, \varphi2)$, $(\varphi1+x, \varphi2)$, $(\varphi1, \varphi2+x)$, $(\varphi1+x, \varphi2+x)$ conformation, calculate the QM energy, if ideally coupled, $E(\varphi1\pm x, \varphi2+x)=E(\varphi1, \varphi2+x)+E(\varphi1+x, \varphi2)-E(\varphi1, 92)$; take a difference between an ideal value and an actual calculated value of $E(\varphi1+x, \varphi2+x)$ as a standard, set a cutoff value, and judge whether the adjacent dihedral angles are coupled.

In a preferred embodiment, The MM calculation judges the coupling in the MM coupling judgment; carries out MM calculation of the one-dimensional potential energy surface scanning for dihedral angles $\varphi1$ and $\varphi2$ respectively, with one dihedral angle being restrained, set a cutoff value by using the fluctuation range of other dihedral angles to determine whether the adjacent dihedral angles are coupled.

In a preferred embodiment, a cutoff value set in the QM coupling judgment module or an absolute deviation of the cutoff value set in the MM coupling judgment module is controlled within 2 kcal/mol or a relative deviation is controlled within 5%, and the interval change is 20-40 degrees. If the coverage degree of 80% or above, it is judged as good, a coverage between 60% and 80% is judged as medium, and a coverage below 60% is judged as poor.

The above-mentioned potential energy surface scanning method and system for the analysis of molecular conformational space finally adopts different conformational scanning methods for different molecules according to the situation, which has high flexibility, which can not only take into account the calculation efficiency, but also ensure the accuracy, and retain the molecular conformation to the greatest extent for important conformations in space, the scanning results can more accurately reflect the conformational space of molecules; multiple complex standards are introduced and adopted to determine whether adjacent dihedral angles are coupled; the relatively fast QM fetching point and MM calculation are used to provide a basis for the subsequent relatively time-consuming QM potential energy surface scanning decision.

DESCRIPTION OF THE PREFERRED EMBODIMENTS

Figure 1:
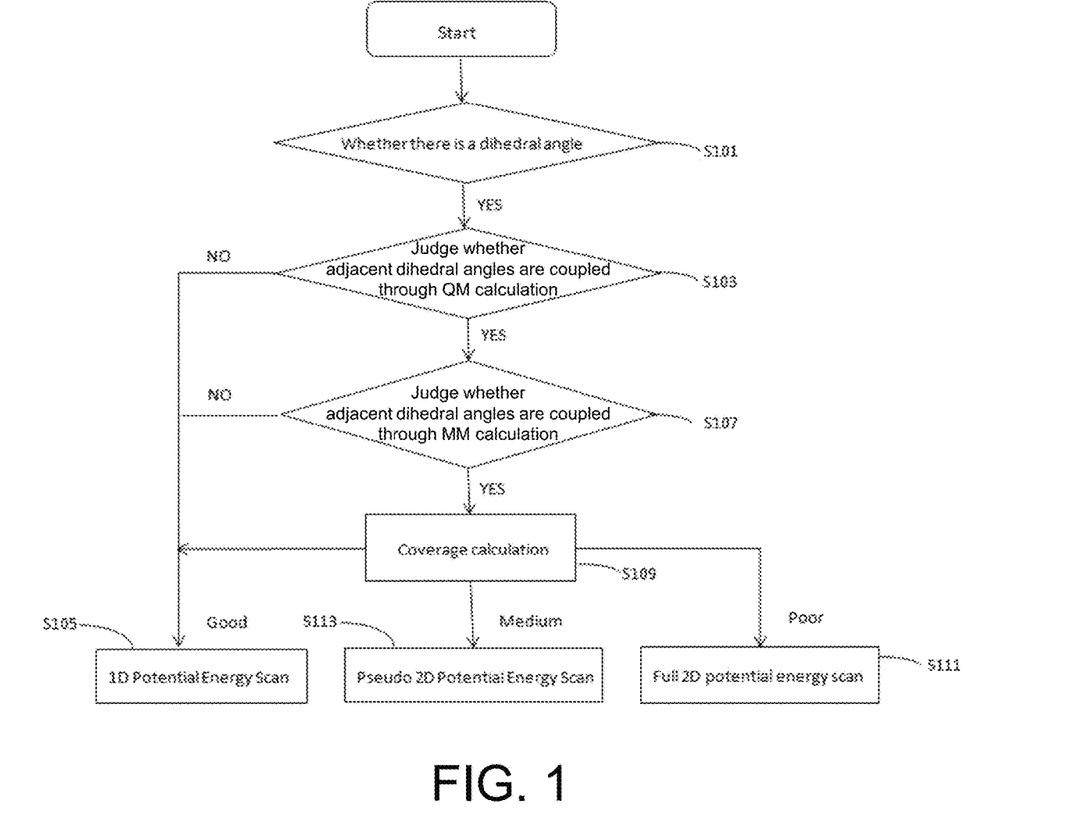
FIG. 1 is a flowchart of a potential energy surface scanning method for the analysis of molecular conformational space according to an embodiment of this invention.
Figure 2:
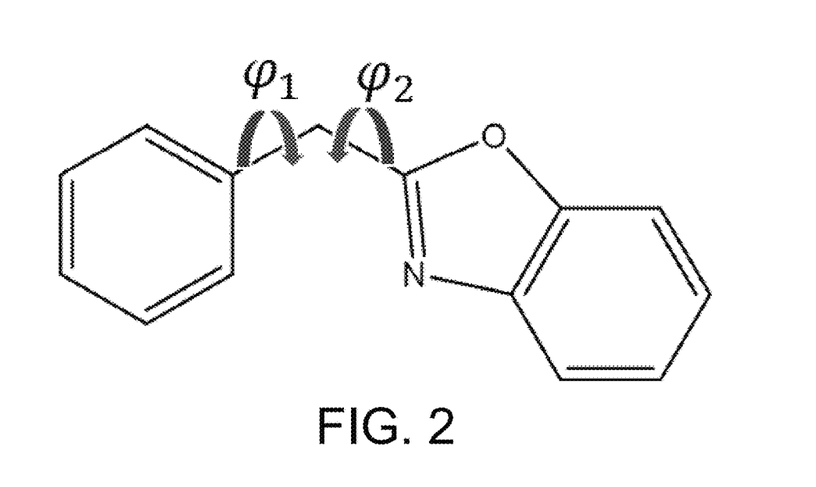
FIG. 2 is a schematic diagram of adjacent dihedral angles according to an embodiment of this invention.

As shown in FIG. 1 and FIG. 2, a potential energy surface scanning method for the analysis of molecular conformational space according to an embodiment of this invention includes the following steps:

Step S101, Adjacent dihedral angle judgment: judge whether a given molecule for analysis has adjacent dihedral angles (as shown in FIG. 2);

Step S103, QM coupling judgment: if it is judged that there are adjacent dihedral angles, judge whether the adjacent dihedral angles are coupled through QM (Quantum Mechanics) calculation, If the QM calculation judges that they are not coupled, go to Step S105:

One-dimensional potential energy scan: restrain one dihedral angle from −180° to +180° at a set interval, and relax the other dihedral angle, scan to obtain the one-dimensional potential energy surface of the molecule.

If the QM calculation judges the coupling, go to Step S107:

MM coupling judgment: MM calculation judges whether the adjacent dihedral angles are coupled.

If MM calculation judges that the adjacent dihedral angles are not coupled, then go to Step S105:

One-dimensional potential energy surface scan: restrain one dihedral angle to change from −180° to +180° at a set interval and relax the other dihedral angle, scan to obtain the one-dimensional potential energy surface of the molecule.

If the MM calculation judges that the adjacent dihedral angles are coupled, then go to step S109 for coverage calculation: calculate a coverage of extreme points on a two-dimensional potential energy surface by a combination of the extreme points obtained by scanning individual one-dimensional potential energy surface of the two dihedral angles according to the MM scanning result; divide coverage levels according to different coverage or coverage ratios as: good, medium and poor.

If the calculated combinations of the extreme points on the two one-dimensional potential energy surfaces have a good coverage for the two-dimensional potential energy surface extreme points, then go to step S105 for one-dimensional potential energy surface scan: restrain one dihedral angle to change from −180° to +180° at a set interval and relax the other dihedral angle, scan to obtain the one-dimensional potential energy surface of the molecule.

If the one-dimensional potential energy surface extreme point combination has a poor coverage of the two-dimensional potential energy surface extreme point in the coverage calculation of step S109, then perform a full two-dimensional potential energy surface scan in step S111: restrain the two adjacent dihedral angles simultaneously, and obtain all the combinations of the two from −180° to +180°.

If the one-dimensional potential energy surface extreme point combination has a medium coverage of the two-dimensional potential energy surface extreme point in the coverage calculation of step S109, then go to step 113 to scan a pseudo-two-dimensional potential energy surface: for two adjacent dihedral angles, restrain only one angle change from −180° to +180°, and, at the same time, the other dihedral angle takes two different starting angle values as starting structures to scan along the potential energy surface of the same dihedral angle.

QM (Quantum Mechanics) calculations can be calculated using quantum chemistry software, input molecular coordinates and other information, and calculate the energy and other information of molecules through the principles of quantum mechanics. Take a point in the molecular conformation space to calculate the energy of several conformations.

For example, for the angle values of two adjacent dihedral angles to take the initial value as (−120°, 20°) with an interval of 20°, the actual points can be (−120°, 20°), (−100°, 20°), (−120°, 40°), (−100°, 40°), calculate the energy of these four conformations by QM, denoted as E1, E2, E3, E4, then $\Delta E = E4 + E1 - E2 - E3$ can be used as coupling judgment standard. The cutoff value for coupling judgment can be set based on experience or a large number of laws summarized by big data statistical analysis.

MM (Molecular Mechanics, molecular mechanics) calculations can use molecular mechanics software, input molecular coordinates and other information, and calculate the molecular energy and other information through the principles of molecular mechanics. The interval of the interval change can be set freely and flexibly according to actual use. The smaller the interval degree, the greater the amount of calculation (more time-consuming and more computing resources are consumed), and the more accurate the results can be. On the contrary, the larger the interval degree, the smaller the calculation amount and the result obtained is relatively inaccurate. For example, it can be set at about 20-40 degrees, and further preferably at about 30 degrees.

Further, a cutoff value set in the QM coupling judgment or an absolute deviation of the cutoff value set in the MM coupling judgment of this embodiment is controlled within 2 kcal/mol and the relative deviation is controlled within 5%. If the coverage is 80% and above, it is judged as good, if the coverage is between 60% and 80%, it is judged as medium, and if the coverage is below 60%, it is judged as poor.

Further, in the QM coupling judgment of this embodiment, the QM calculation judgment is that for a molecule with adjacent dihedral angles, take the points ($\varphi1$, $\varphi2$), ($\varphi1+x$, $\varphi2$), ($\varphi1$, $92+x$), ($\varphi1+x$, $\varphi2+x$) and other conformations, calculate the QM energy. In the ideal coupling case, $E(\varphi1+x, \varphi2+x) = E(\varphi1, \varphi2+x) + E(\varphi1+x, \varphi2) - E(\varphi1, \varphi2)$, take the difference between the ideal value of $E(\varphi1+x, \varphi2+x)$ and the actual calculated value as the standard to set the cutoff value, and judge whether the adjacent dihedral angles are coupled.

Further, in the MM coupling judgment of this embodiment, the MM calculation judges the coupling, and the MM calculation of the one-dimensional potential energy surface scan is performed on the dihedral angles of $\varphi1$ and $\varphi2$ respectively; restraining one dihedral angle, and take the change amplitude of the other dihedral angle as standard, set the cutoff value to judge whether adjacent dihedral angles are coupled.

The one-dimensional (1D) potential energy surface scan of this embodiment is restraining one dihedral angle from −180° to +180° at a certain interval with other dihedral angles are not restricted to obtain the one-dimensional potential energy surface of the molecule.

In the full two-dimensional (2D) scanning of this embodiment: two adjacent dihedral angles are simultaneously restricted, and all combinations of the two from −180° to +180° are obtained. For example, if the scanning interval of the potential energy surface is 30°, for two adjacent dihedral angles, one-dimensional potential energy surface scanning needs to calculate 24 constellations, and full two-dimensional scanning needs to calculate 144 constellations.

For two adjacent dihedral angles, if one dihedral angle is changed, the positions of the maximum and minimum points on the potential energy surface of the other dihedral angle do not change accordingly, the two dihedral angles are not coupled. On the contrary, they are coupled. If two adjacent dihedral angles are not coupled, the approximate two-dimensional potential energy surface can be obtained by combining the one-dimensional potential energy surface combination of the two dihedral angles; if coupled, the one-dimensional potential energy surface combination cannot reflect the true condition of the two-dimensional potential energy surface, and a two-dimensional potential energy surface scan is required.

Figure 3:
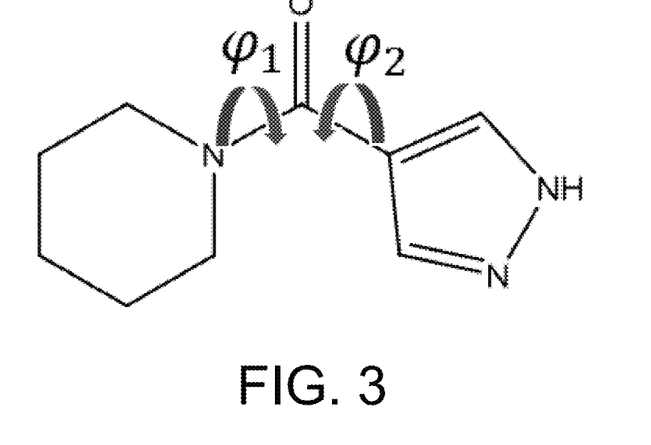
FIG. 3 is a schematic diagram of adjacent dihedral angles in a preferred embodiment of this invention.
Figure 4:
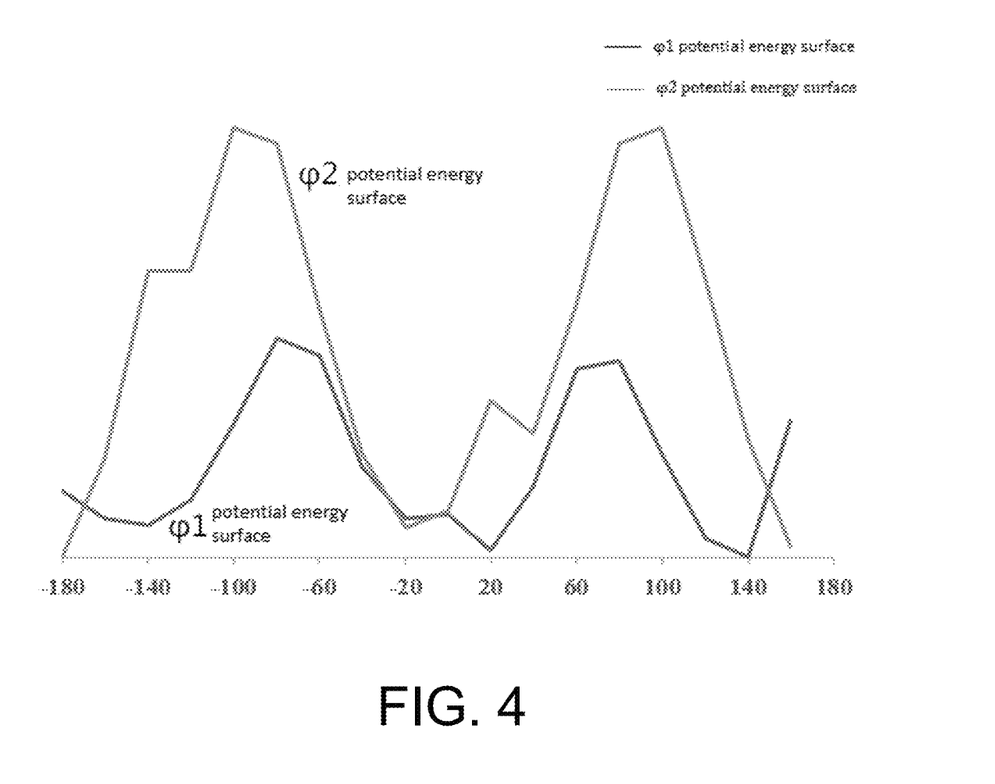
FIG. 4 is a one-dimensional potential energy surface MM scanning curve of a preferred embodiment of this invention.
Figure 5:
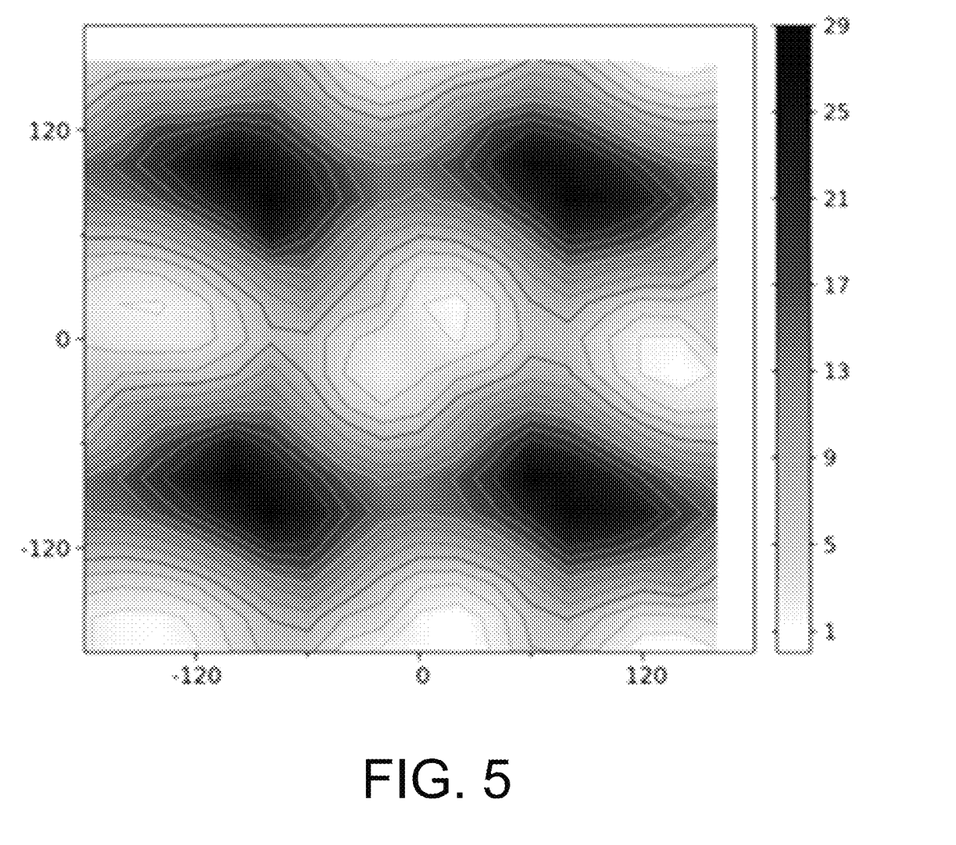
FIG. 5 is a two-dimensional potential energy surface MM scanning curve of a preferred embodiment of this invention.

As shown in FIGS. 3 to 5, in further specific embodiments: if the cutoff value of QM coupling judgment is empirically set to 4, the cutoff value of MM coupling judgment is (20, 20). The coverage of one-dimensional potential energy surface combination extreme points to two-dimensional potential energy surface takes 80% as cutoff value. As shown in FIG. 3, take this molecule as an example: take the points $\varphi1$ and $\varphi2$ at 20° intervals as (−120, 20), (−100, 20), (−120 40), (−100, 40), the calculated QM energy coupling value of the corresponding conformation is 6.7, so they are judged to be coupled by QM calculation. Calculate the MM coupling value by scanning the two one-dimensional potential energy surfaces again as (7, 24), which is judged to be uncoupled. Carry out the MM calculation scanning of the one-dimensional potential energy surface and the two-dimensional potential energy surface calculation respectively, and obtain the two potential energy surface curves of FIG. 4 and the two-dimensional potential energy of FIG. 5. The potential energy surface curve in FIG. 4 shows that the two dihedral angles have minimum points at −140°, 20°, −160°, −180°, and −20°. Then through the combinations of one-dimensional potential energy surfaces, Minimum points of the two dihedral angles can be obtained at the following 6 points: (−140°, −180°), (−140°, −20°), (20°, −180°), (20°, −20°), (−160°, −180°), (−160°, −20°). Then according to the two-dimensional potential energy surface diagram of FIG. 5, there are a total of 6 minimum points, all of which are consistent with the above. Therefore, the coverage of the one-dimensional potential energy surface combination of the molecule on the two-dimensional potential energy surface is 6/6=100%, so the pseudo-two-dimensional potential energy surface scan is performed. The judgment of the coverage situation can also be set relatively flexibly based on rationality. Preferably, 80% and 60% can be used in practice as cutoff values judged to be good and medium respectively.

The scanning method of this embodiment rotates the dihedral angle of the molecule to fix it at different angles to obtain different conformations of the molecule, and calculate the energy of these conformations respectively. The MM calculation software in this embodiment is AMBER. Other software can also be used according to actual needs, and internally developed software can also be used to realize the functions of this implementation.

A potential energy surface scanning system for the analysis of molecular conformational space according to an embodiment of this invention includes:

Adjacent dihedral angle judgment module: judge whether a given molecule has adjacent dihedral angles;

QM coupling judgment module: if it is judged that there are adjacent dihedral angles, judge whether the adjacent dihedral angles are coupled through QM calculation;

If the QM calculation judges that they are not coupled, perform an one-dimensional potential energy scan: restrain one dihedral angle from −180° to +180° at a set interval, and relax the other dihedral angle, to obtain the one-dimensional potential energy surface of the molecule.

If the QM calculation judges that they are coupled, then perform a MM coupling judgment: the MM calculation judges whether the adjacent dihedral angles are coupled;

If MM calculation judges that the adjacent dihedral angles are not coupled, then perform one-dimensional potential energy surface scan: restrain one dihedral angle to change from −180° to +180° at a set interval and relax the other dihedral angle, scan to obtain the one-dimensional potential energy surface of the molecule.

If the MM calculation judges that the adjacent dihedral angles are coupled, then perform a coverage calculation: calculate a coverage of extreme points on a two-dimensional potential energy surface by a combination of the extreme points obtained by scanning individual one-dimensional potential energy surface of the two dihedral angles according to the MM scanning result; divide coverage levels according to different coverage or coverage ratios as: good, medium and poor.

If the calculated combinations of the extreme points on the one-dimensional potential energy surfaces have a good coverage for the two-dimensional potential energy surface, then perform the one-dimensional potential energy surface scan: restrain one dihedral angle to change from −180° to +180° at a set interval and relax the other dihedral angle, scan to obtain the one-dimensional potential energy surface of the molecule.

If the combinations of the extreme points on the one-dimensional potential energy surface have a poor coverage of the extreme points on the two-dimensional potential energy surface in the coverage calculation calculated in the coverage calculation module, then perform a full two-dimensional potential energy surface scan: restrain two adjacent dihedral angles simultaneously, and obtain all the combinations of the two from −180° to +180°.

If the combinations of the extreme points on the one-dimensional potential energy surface extreme point combination has a medium coverage of the two-dimensional potential energy surfaces have a medium coverage of the extreme points on the two dimensional potential energy surface have a medium coverage of the extreme points on the two-dimensional potential energy surface in the coverage calculation calculated in the coverage calculation module, then proceed a pseudo-two-dimensional potential energy surface: for two adjacent dihedral angles, restrain only one angle to change from −180° to +180°, and, at the same time, the other dihedral angle takes two different starting angle values as the starting structure. It is two potential energy surfaces scanning along the same dihedral angle.

Further, in the QM coupling judgment of this embodiment, the QM calculation judgment is that for a molecule with adjacent dihedral angles by a spacing such as x°, then the QM energies are calculated by 4 conformers, $(\varphi1, \varphi2)$, $(\varphi1+x, \varphi2)$, $(\varphi1, \varphi2+x)$, $(\varphi1+x, \varphi2+x)$. In the ideal coupling case, $E(\varphi1+x, \varphi2+x)=E(\varphi1, \varphi2+x)+E(\varphi1+x, \varphi2)−E(\varphi1, \varphi2)$, take a difference between an ideal value of $E(\varphi1+x, \varphi2+x)$ and an actual calculated value as a standard to set a cutoff value, and judge whether the adjacent dihedral angles are coupled.

The MM calculation judges the coupling in MM coupling judgment module, and carries out the MM calculation of the one-dimensional potential energy surface scan for dihedral angles of $\varphi1$ and $\varphi2$ respectively; with one dihedral angle being restrained, set a cutoff value by using the fluctuation range of the other dihedral angles to determine whether adjacent dihedral angles are coupled.

In the preferred embodiment, an absolute deviation of the cutoff value set in the QM coupling judgment or the cutoff value set in the MM coupling judgment of this embodiment is controlled within 2 kcal/mol and a relative deviation is controlled within 5%, if the coverage is 80% and above, it is judged as good, if the coverage is between 60% and 80%, it is judged as medium, and if the coverage is below 60%, it is judged as poor.

The set-level potential energy surface scanning decision tree of this invention adopts different conformational scanning methods for different molecules according to the situation. It has high flexibility, can take into account the calculation efficiency and ensure the accuracy, and retain the important conformations in the molecular conformation space to the maximum extent. The result can more accurately reflect the conformational space of the molecule. The decision tree introduces and adopts multiple and complex criteria to determine whether adjacent dihedral angles are coupled, and uses relatively fast QM points and MM calculations to provide a basis for the subsequent relatively time-consuming QM potential energy surface scanning decision.

Taking the above-mentioned ideal embodiments based on this application as enlightenment, and based on the above description, the relevant staff can make various changes and modifications without departing from the technical idea of this application. The technical scope of this application is not limited to the content in the specification, and its technical scope must be determined according to the scope of the claims.

Those skilled in the art should understand that the embodiments of this application may be provided as methods, systems, or computer program products. Therefore, this application may adopt the form of a complete hardware embodiment, a complete software embodiment, or an embodiment combining software and hardware. Moreover, this application may adopt the form of a computer program product implemented on one or more computer-usable storage media (including but not limited to disk storage, CD-ROM, optical storage, etc.) containing computer-usable program codes.

This application is described with reference to flowcharts and/or block diagrams of methods, equipment (systems), and computer program products according to embodiments of this application.

It should be understood that each process and/or block in the flowchart and/or block diagram, and the combination of processes and/or blocks in the flowchart and/or block diagram can be realized by computer program instructions.

These computer program instructions can be provided to the processor of a general-purpose computer, a special-purpose computer, an embedded processor, or other programmable data processing equipment to generate a machine, so that the instructions executed by the processor of the computer or other programmable data processing equipment can generate a device to realize the functions specified in one process or multiple processes in the flowchart and/or one block or multiple blocks in the block diagram.

These computer program instructions can also be stored in a computer-readable memory that can guide a computer or other programmable data processing equipment to work in a specific manner, so that the instructions stored in the computer-readable memory can produce products with command device. The command device can realize the functions specified in one process or multiple processes in the flowchart and/or one block or multiple blocks in the block diagram.

These computer program instructions can also be loaded on a computer or other programmable data processing equipment, so that a series of operation steps are executed on the computer or other programmable equipment to produce computer-implemented processing. Thereby, the instructions executed on the computer or other programmable devices provide steps for implementing the functions specified in one or more processes in the flowchart and/or one block or more in the block diagram.

What is claimed is:

1. A potential energy surface scanning method for the analysis of molecular conformational space, implemented by a processor, comprising:
   adjacent dihedral angle judgment: judge whether a given molecule has adjacent dihedral angles;
   quantum mechanics (QM) coupling judgment: if it is judged that there are adjacent dihedral angles, judge whether the adjacent dihedral angles are coupled through QM calculation,
   if the QM calculation judges that the adjacent dihedral angles are not coupled, perform an one-dimensional potential energy scan: restrain one dihedral angle from −180° to +180° at a set interval, relax the other dihedral angle, scan to obtain an one-dimensional potential energy surface of the molecule;
   if the QM calculation judges that the adjacent dihedral angles are coupled, then perform a molecular mechanics (MM) coupling judgment: the MM calculation judges whether the adjacent dihedral angles are coupled;
   if MM calculation judges that the adjacent dihedral angles are not coupled, then perform the one-dimensional potential energy surface scan: restrain one dihedral angle to change from −180° to +180° at a set interval and relax the other dihedral angle, scan to obtain the one-dimensional potential energy surface of the molecule;
   if the MM calculation judges that the adjacent dihedral angles are coupled, then calculate a coverage of extreme points on a two-dimensional potential energy surface by a combination of the extreme points obtained by scanning individual one-dimensional potential energy surfaces of the two dihedral angles according to a MM scanning result, and determine a coverage level corresponding to the calculated coverage at least from a first level and a second level; wherein the coverage level corresponding to the calculated coverage is the first level if the calculated coverage is not smaller than a first preset value, the coverage level corresponding to the calculated coverage is the second level if the calculated coverage is smaller than a second preset value which is smaller than the first preset value;
   if the coverage level corresponding to the calculated coverage is the first level, then perform the one-dimensional potential energy surface scan: restrain one dihedral angle to change from −180° to +180° at a set interval and relax the other dihedral angle, scan to obtain the one-dimensional potential energy surface of the molecule;
   if the coverage level corresponding to the calculated coverage is not the first level, then perform a potential energy surface scan different from the one-dimensional potential energy surface scan.

2. The potential energy surface scanning method for molecular conformational space analysis according to claim 1, wherein if the coverage level corresponding to the calculated coverage is the second level, then perform a full two-dimensional potential energy surface scan: restrain the two adjacent dihedral angles simultaneously, and obtain all the combinations of the two from −180° to +180°.

3. The potential energy surface scanning method for molecular conformational space analysis according to claim 2, wherein in the QM coupling judgment: for the given molecule with adjacent dihedral angles by a spacing such as x°, then the QM energies are calculated by 4 conformers, (φ1, φ2), (φ1+x, φ2), (φ1, φ2+x), (φ1+x, φ2+x), if ideally coupled, E(φ1+x, φ2+x)=E(φ1, φ2+x)+E(φ1+x, φ2)−E(φ1, φ2); take a difference between an ideal value and an actual calculated value of E(φ1+x, φ2+x) as a standard, set a cutoff value, and judge whether the adjacent dihedral angles are coupled.

4. The potential energy surface scanning method for molecular conformational space analysis according to claim 2, wherein the MM calculation judges the coupling in the MM coupling judgment; carry out MM calculations of the one-dimensional potential energy surface scanning for dihedral angles φ1 and φ2 respectively, with one dihedral angle being restrained, set a cutoff value by using the fluctuation range of other dihedral angles to determine whether the adjacent dihedral angles are coupled.

5. The potential energy surface scanning method for molecular conformational space analysis according to claim 2, wherein a cutoff value set in the QM coupling judgment or an absolute deviation of the cutoff value set in the MM coupling judgment is controlled at 2 kcal/mol or a relative deviation is controlled within 5%, the interval change is 20-40 degrees, the first preset value is 80% and the second preset value is 60%.

6. The potential energy surface scanning method for molecular conformational space analysis according to claim 1, wherein if the coverage level corresponding to the calculated coverage is a third level, then scan a pseudo-two-dimensional potential energy surface: for two adjacent dihedral angles, restrain only one angle to change from −180° to +180°, and, at the same time, the other dihedral angle takes two different starting angle values as starting structures to scan along the potential energy surface of the same dihedral angle;
wherein the coverage level corresponding to the calculated coverage is the third level if the calculated coverage is between the first preset value and the second preset value.

7. The potential energy surface scanning method for molecular conformational space analysis according claim 6, wherein in the QM coupling judgment: for the given molecule with adjacent dihedral angles by a spacing such as x°, then the QM energies are calculated by 4 conformers, (φ1, φ2), (φ1+x, φ2), (φ1, φ2+x), (φ1+x, φ2+x), if ideally coupled, E(φ1+x, φ2+x)=E(φ1, φ2+x)+E(φ1+x, φ2)−E(φ1, φ2); take a difference between an ideal value and an actual calculated value of E(φ1+x, φ2+x) as a standard, set a cutoff value, and judge whether the adjacent dihedral angles are coupled.

8. The potential energy surface scanning method for molecular conformational space analysis according to claim 6, wherein the MM calculation judges the coupling in the MM coupling judgment; carry out MM calculations of the one-dimensional potential energy surface scanning for dihedral angles φ1 and φ2 respectively, with one dihedral angle being restrained, set a cutoff value by using the fluctuation range of other dihedral angles to determine whether the adjacent dihedral angles are coupled.

9. The potential energy surface scanning method for molecular conformational space analysis according to claim 6, wherein a cutoff value set in the QM coupling judgment or an absolute deviation of the cutoff value set in the MM coupling judgment is controlled at 2 kcal/mol or a relative deviation is controlled within 5%, the interval change is 20-40 degrees, the first preset value is 80% and the second preset value is 60%.

10. The potential energy surface scanning method for molecular conformational space analysis according to claim 1, wherein in the QM coupling judgment: for the given molecule with adjacent dihedral angles by a spacing such as x°, then the QM energies are calculated by 4 conformers, (φ1, φ2), (φ1+x, φ2), (φ1, φ2+x), (φ1+x, φ2+x), if ideally coupled, E(φ1+x, φ2+x)=E(φ1, φ2+x)+E(φ1+x, φ2)−E(φ1, φ2); take a difference between an ideal value and an actual calculated value of E(φ1+x, φ2+x) as a standard, set a cutoff value, and judge whether the adjacent dihedral angles are coupled.

11. The potential energy surface scanning method for molecular conformational space analysis according to claim 1, wherein the MM calculation judges the coupling in the MM coupling judgment; carry out MM calculations of the one-dimensional potential energy surface scanning for dihedral angles φ1 and φ2 respectively, with one dihedral angle being restrained, set a cutoff value by using the fluctuation range of other dihedral angles to determine whether the adjacent dihedral angles are coupled.

12. The potential energy surface scanning method for molecular conformational space analysis according to claim 1, wherein a cutoff value set in the QM coupling judgment or an absolute deviation of the cutoff value set in the MM coupling judgment is controlled at 2 kcal/mol or a relative deviation is controlled within 5%, the interval change is 20-40 degrees, the first preset value is 80% and the second preset value is 60%.

13. A potential energy surface scanning system for analysis of molecular conformational space, comprising:
a memory; and
a processor, coupled to the memory, comprising:
adjacent dihedral angle judgment module: judge whether a given molecule has adjacent dihedral angles;
quantum mechanics (QM) coupling judgment module: if it is judged that there are adjacent dihedral angles, judge whether the adjacent dihedral angles are coupled through QM calculation;
if the QM calculation judges that the adjacent dihedral angles are not coupled, perform an one-dimensional potential energy scan: restrain one dihedral angle from −180° to +180° at a set interval, and relax the other dihedral angle, scan to obtain the one-dimensional potential energy surface of the molecule;
if the QM calculation judges that the adjacent dihedral angles are coupled, then perform a molecular mechanics (MM) coupling judgment: the MM calculation judges whether the adjacent dihedral angles are coupled;
if MM calculation judges that the adjacent dihedral angles are not coupled, then perform the one-dimensional potential energy surface scan: restrain one dihedral angle to change from −180° to +180° at a set interval and relax the other dihedral angle, scan to obtain the one-dimensional potential energy surface of the molecule;
if the MM calculation judges that the adjacent dihedral angles are coupled, then perform a coverage calculation: calculate a coverage of extreme points on a two-dimensional potential energy surface by a combination of the extreme points obtained by scanning individual one-dimensional potential energy surface of the two dihedral angles according to a MM scanning result, and determine a coverage level corresponding to the calculated coverage at least from a first level and a second level; wherein the coverage level corresponding to the calculated coverage is the first level if the calculated coverage is not smaller than a first preset value, the coverage level corresponding to the calculated coverage is the second level if the calculated coverage is smaller than a second preset value which is equal to or smaller than the first preset value;

if the coverage level corresponding to the calculated coverage is the first level, then perform the one-dimensional potential energy surface scan: restrain one dihedral angle to change from −180° to +180° at a set interval and relax the other dihedral angle, scan to obtain the one-dimensional potential energy surface of the molecule;

if the coverage level corresponding to the calculated coverage is not the first level, then perform a potential energy surface scan different from the one-dimensional potential energy surface scan.

14. The potential energy surface scanning system for molecular conformational space analysis according to claim 13, wherein the second preset value is smaller than the first preset value, and if the coverage level corresponding to the calculated coverage calculated is the second level, then perform a full two-dimensional potential energy surface scan: restrain two adjacent dihedral angles simultaneously, and obtain all combinations of the two from −180° to +180°.

15. The potential energy surface scanning system for molecular conformational space analysis according to claim 14, wherein a method of the QM coupling judgment module is: for a molecule with adjacent dihedral angles by a spacing such as x°, then the QM energies are calculated by 4 conformers, ($\varphi 1$, $\varphi 2$), ($\varphi 1+x$, $\varphi 2$), ($\varphi 1$, $\varphi 2+x$), ($\varphi 1+x$, $\varphi 2+x$), if ideally coupled, $E(\varphi 1+x, \varphi 2+x)=E(\varphi 1, \varphi 2+x)+E(\varphi 1+x, \varphi 2)-E(\varphi 1, \varphi 2)$; take a difference between an ideal value and an actual calculated value of $E(\varphi 1+x, \varphi 2+x)$ as a standard, set a cutoff value, and judge whether the adjacent dihedral angles are coupled;

the MM calculation judges the coupling in the MM coupling judgment, carries out MM calculation of the one-dimensional potential energy surface scanning for dihedral angles $\varphi 1$ and $\varphi 2$ respectively, with one dihedral angle being restrained, set a cutoff value by using the fluctuation range of other dihedral angles to determine whether the adjacent dihedral angles are coupled;

a cutoff value set in the QM coupling judgment module or an absolute deviation of the cutoff value set in the MM coupling judgment module is controlled within 2 kcal/mol or a relative deviation is controlled within 5%, the interval change is 20-40 degrees, the first preset value is 80% and the second preset value is 60%.

16. The potential energy surface scanning system for molecular conformational space analysis according to claim 13, wherein the second preset value is smaller than the first preset value, and if the coverage level corresponding to the calculated coverage calculated is a third level, then proceed a pseudo-two-dimensional potential energy surface scanning module: for two adjacent dihedral angles, restrain only one angle to change from −180° to +180°, and, at the same time, the other dihedral angle takes two different starting angle values as starting structures to scan along the potential energy surface of the same dihedral angle;

wherein the coverage level corresponding to the calculated coverage is the third level if the calculated coverage is between the first preset value and the second preset value.

17. The potential energy surface scanning system for molecular conformational space analysis according to claim 16, wherein a method of the QM coupling judgment module is: for a molecule with adjacent dihedral angles by a spacing such as x°, then the QM energies are calculated by 4 conformers, ($\varphi 1$, $\varphi 2$), ($\varphi 1+x$, $\varphi 2$), ($\varphi 1$, $\varphi 2+x$), ($\varphi 1+x$, $\varphi 2+x$), if ideally coupled, $E(\varphi 1+x, \varphi 2+x)=E(\varphi 1, \varphi 2+x)+E(\varphi 1+x, \varphi 2)-E(\varphi 1, \varphi 2)$; take a difference between an ideal value and an actual calculated value of $E(\varphi 1+x, \varphi 2+x)$ as a standard, set a cutoff value, and judge whether the adjacent dihedral angles are coupled;

the MM calculation judges the coupling in the MM coupling judgment, carries out MM calculation of the one-dimensional potential energy surface scanning for dihedral angles $\varphi 1$ and $\varphi 2$ respectively, with one dihedral angle being restrained, set a cutoff value by using the fluctuation range of other dihedral angles to determine whether the adjacent dihedral angles are coupled;

a cutoff value set in the QM coupling judgment module or an absolute deviation of the cutoff value set in the MM coupling judgment module is controlled within 2 kcal/mol or a relative deviation is controlled within 5%, the interval change is 20-40 degrees, the first preset value is 80% and the second preset value is 60%.

18. The potential energy surface scanning system for molecular conformational space analysis according to claim 7, wherein a method of the QM coupling judgment module is: for a molecule with adjacent dihedral angles by a spacing such as x°, then the QM energies are calculated by 4 conformers, ($\varphi 1$, $\varphi 2$), ($\varphi 1+x$, $\varphi 2$), ($\varphi 1$, $\varphi 2+x$), ($\varphi 1+x$, $\varphi 2+x$), if ideally coupled, $E(\varphi+x, \varphi 2+x)=E(\varphi 1, \varphi 2+x)+E(\varphi 1+x, \varphi 2)-E(\varphi 1, \varphi 2)$; take a difference between an ideal value and an actual calculated value of $E(\varphi 1+x, (\varphi 2+x)$ as a standard, set a cutoff value, and judge whether the adjacent dihedral angles are coupled;

the MM calculation judges the coupling in the MM coupling judgment, carries out MM calculation of the one-dimensional potential energy surface scanning for dihedral angles $\varphi 1$ and $\varphi 2$ respectively, with one dihedral angle being restrained, set a cutoff value by using the fluctuation range of other dihedral angles to determine whether the adjacent dihedral angles are coupled;

a cutoff value set in the QM coupling judgment module or an absolute deviation of the cutoff value set in the MM coupling judgment module is controlled within 2 kcal/mol or a relative deviation is controlled within 5%, the interval change is 20-40 degrees, the first preset value is 80% and the second preset value is 60%.

19. A potential energy surface scanning method for the analysis of molecular conformational space, implemented by a processor, comprising:

judging whether adjacent dihedral angles of a given molecule are coupled;

if it is judged that adjacent dihedral angles of a given molecule are not coupled, performing an one-dimensional potential energy surface scan;

if it is judged that adjacent dihedral angles of a given molecule are coupled, calculating a coverage of extreme points on a two-dimensional potential energy surface by a combination of extreme points obtained by scanning individual one-dimensional potential energy surfaces of the two dihedral angles, determining a corresponding scan method based on the calculated coverage from a plurality of potential energy surface scan methods, and performing the corresponding scan method.

20. The potential energy surface scanning method for molecular conformational space analysis according to claim 19, wherein the plurality of potential energy surface scan methods comprises one-dimensional potential energy surface scan and at least one of full two-dimensional potential energy surface scan and pseudo-two-dimensional potential energy surface scan.

* * * * *